(12) United States Patent
Gatto

(10) Patent No.: US 6,878,149 B2
(45) Date of Patent: *Apr. 12, 2005

(54) APPARATUS AND METHOD FOR INTRADUCTAL ABALATION

(75) Inventor: Dominick L. Gatto, Branford, CT (US)

(73) Assignee: Acueity, Inc., Palo Alto, CA (US)

( * ) Notice: Subject to any disclaimer, the term of this patent is extended or adjusted under 35 U.S.C. 154(b) by 150 days.

This patent is subject to a terminal disclaimer.

(21) Appl. No.: 10/112,954

(22) Filed: Apr. 2, 2002

(65) Prior Publication Data

US 2003/0187324 A1 Oct. 2, 2003

Related U.S. Application Data

(63) Continuation-in-part of application No. 10/104,016, filed on Mar. 25, 2002.

(51) Int. Cl.[7] ............................................... A61B 18/18
(52) U.S. Cl. ........................ 606/46; 600/104; 600/153
(58) Field of Search ......................... 600/104, 128–130, 600/153, 156; 606/41, 45–50

(56) References Cited

U.S. PATENT DOCUMENTS

| | | | | |
|---|---|---|---|---|
| 3,297,022 A | * | 1/1967 | Wallace | 600/172 |
| 5,083,549 A | * | 1/1992 | Cho et al. | 600/108 |
| 5,107,513 A | | 4/1992 | Sagie et al. | |
| 5,843,028 A | * | 12/1998 | Weaver et al. | 604/514 |
| 5,861,002 A | * | 1/1999 | Desai | 606/210 |
| 6,221,622 B1 | | 4/2001 | Love | |
| 6,500,114 B1 | * | 12/2002 | Petitto et al. | 600/156 |
| 2003/0055315 A1 | * | 3/2003 | Gatto et al. | 600/114 |
| 2003/0181823 A1 | * | 9/2003 | Gatto | 600/564 |
| 2003/0187324 A1 | * | 10/2003 | Gatto | 600/101 |
| 2003/0187427 A1 | * | 10/2003 | Gatto | 606/15 |
| 2003/0199726 A1 | * | 10/2003 | Gatto | 600/3 |

* cited by examiner

Primary Examiner—Michael Peffley
(74) Attorney, Agent, or Firm—Olson & Hierl, Ltd.

(57) ABSTRACT

The invention is directed toward a micro-endoscope assembly for the ablation of tissue in breast ducts comprising a cylindrical guide tube with a distal end defining an internal cylindrical passageway, a first smaller cylindrical tube eccentrically formed in the cylindrical passageway of a smaller diameter than said tube internal cylindrical passageway to receive and guide an endoscope, the smaller cylindrical tube forming together with an inner wall surface of the cylindrical guide tube a second passageway. A energy transmitting probe is mounted in the second passageway and is connected at the distal end of the guide tube with an energy transmitting device. The assembly is inserted into a mammary duct and the interior of the duct is viewed until an abnormality is determined in the duct. The tissue and cells from the abnormality area are ablated, irrigated and aspirated through a suction channel to a collection device.

15 Claims, 3 Drawing Sheets

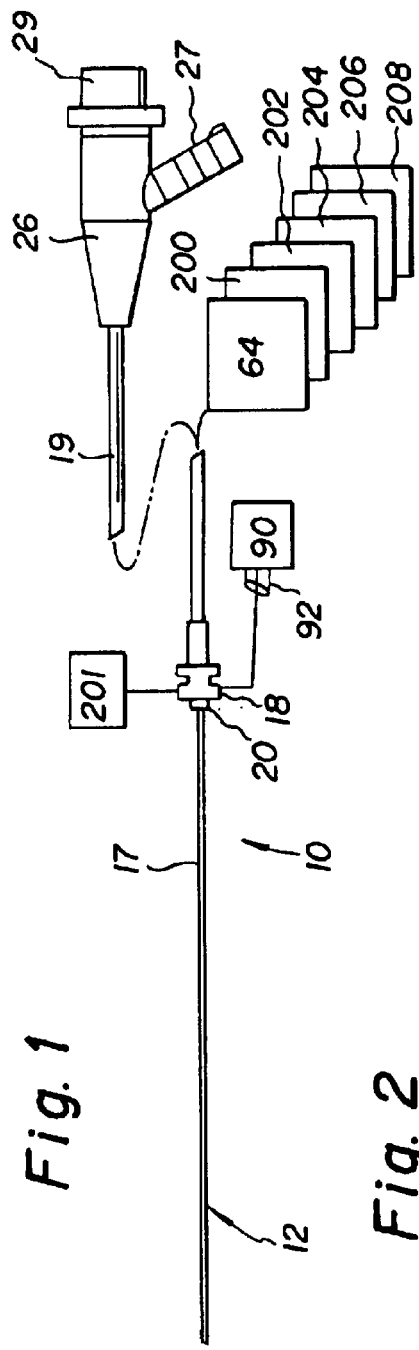
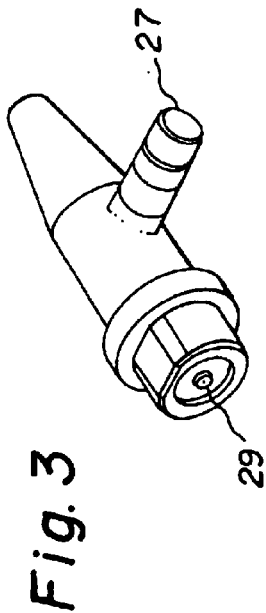
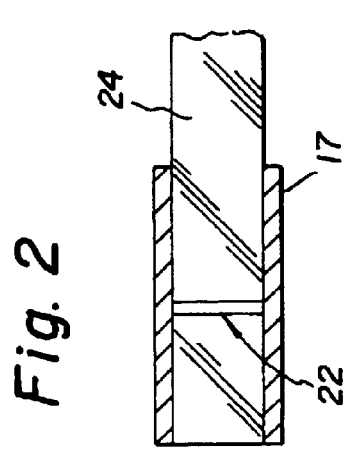
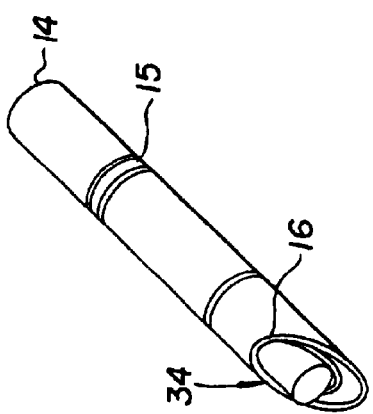

APPARATUS AND METHOD FOR INTRADUCTAL ABALATION

RELATED APPLICATION

This is a continuation-in-part application of U.S. patent application Ser. No. 10/104,016 filed on Mar. 25, 2002 and incorporated herein by reference.

FIELD OF INVENTION

The present invention is generally directed toward the treatment of breast cancer and more specifically toward the ablation of abnormal tissue and cells in the mammary breast ducts of women.

BACKGROUND OF THE INVENTION

A leading disease incurred by women is breast cancer. Breast cancer is the second leading cause of death for women of all ages and the leading cause of death for women aged 25–55. Approximately one in eight women will incur breast cancer in their lifetimes. Approximately 220,000 surgeries are performed annually in the United States with almost 20 percent requiring the complete removal of the breast. The current medical standard for determining breast cancer in women is mammography. For breast cancer detection, other than clinical examination and self-examination, women rely almost exclusively on mammography. It is estimated that more than 30 million mammograms are performed each year in the U.S. alone. When cancer is detected, mammography is so insensitive that typically the average size of the tumor detected is approximately 1.5 cm. At that size, a tumor has probably been growing, undetected, for nearly 8 years on average. In fact, two-thirds of mammographically detected breast cancer is invasive. In addition, mammography is notorious for "false positive" readings, which lead to many unneeded biopsies. However mammography fails to detect up to 20% of breast cancers in women over 50 and up to 40% of breast cancers in younger women. Breast cancer grows slowly but under current techniques such as mammography the average detection is only on cancer growths which have been growing over seven years at which time the growth size of the cancer generally ranges between 1 and 2 cm. Medical researchers have long recognized that nearly all breast cancer originates in the epithelial lining of the mammary duct system. Furthermore, it is well established that, in its early stages, most breast cancer develops very slowly and remains confined to the mammary ducts for up to 7–10 years. If these very early stages of premalignant and malignant disease could be detected and treated while within the mammary duct system, the result would be substantially better treatment outcomes: enhanced survivability, avoidance of chemotherapy and radiation, and breast conservation.

After detection breast cancer is generally treatable in three ways: surgery, radiation and chemotherapy. Surgery and radiation, of course, have risks and disadvantages well known to those skilled in the art. Chemotherapy also can be particularly disadvantageous as, for example, when the drugs involved cause sickness to the patient when they enter the blood stream.

Today's primary treatment of breast cancer is traditional surgery, either mastectomy or lumpectomy with radiation therapy. Surgery is, by definition, invasive and traumatic. Because the exact margins of cancerous growth are difficult to pinpoint, a surgeon may remove more breast tissue than is necessary or not remove enough. Between newly diagnosed breast cancer surgeries and re-excisions, approximately 180,000 lumpectomies are performed each year in the United States.

Mammary Intraductal Ablation (MIA) refers to a procedure in which the lining of the mammary duct is destroyed to control abnormal intraductal pathology that may or may not be related to malignancy. Today, women with positive mammograms, positive biopsies or intraductal atypia (abnormal pathology) often have a choice of watchful waiting, medical therapy, or surgery (lumpectomy and mastectomy). The advancement of new technology and techniques for the treatment of breast disease has not kept pace with other medical areas, particularly in the area of minimally invasive techniques (mammary ductoscopy).

Intraductal ablation is not intended to replace surgery, which is the definitive treatment for most malignant pathology. However, intraductal ablation gives women a choice in their treatment of abnormal intraductal pathology. Women who want permanent relief from the anxiety associated with breast cancer—can choose endoscopic intraductal ablation. Those who are more concerned about preserving the mammary duct or desire an outpatient procedure with minimal morbidity may find that intraductal ablation is the better choice. Women who participate in the decision making process are more likely to be satisfied with their treatment outcome. All women with negative mammograms and abnormal cytology from intraductal assessment in whom neither Tamoxifen nor mastectomy is desired are candidates for intraductal ablation. In addition, those women who have a positive mammogram (micro-calcifications) or biopsy positive DCIS are candidates for MIA.

Physicians must be careful to maintain strict criteria for performing this procedure on women with positive mammograms or intraductal atypia and not on women with advanced stage breast cancer. Intraductal atypia due to systemic disease may be controlled by appropriate therapy of the underlying medical disorder. In most cases, cancerous or pre-cancerous lesions can be treated with intraductal therapies with or without irradiation or chemotherapy.

Benign conditions that can lead to abnormal intraductal assessment include intraductal papilloma, hyperplasia and atypical ductal hyperplasia and these can be removed without requiring invasive surgery. Likewise, hormonal therapies, and pharmaceutical agents (Tamoxifen) may control the growth of intraductal cancerous lesions. Intraductal ablation can be indicated for women who have not responded to medical therapy or choose not to take the agents due to side effects or other personal reasons. All women should have biopsies or intraductal samplings (ravage) that document the presence of atypia or malignant disease before an intraductal ablation is performed. The mammary duct should also be assessed by office ductoscopy to exclude the possibility of intraductal papillomas, which can be treated with a simple resection. In addition, mammary ductoscopy may reveal women who have multi-focal abnormal epithelia tissue and thus may be candidates for more extensive intraductal therapy.

Intraductal techniques are categorized as either "detection" techniques or "ablation" techniques.

The present detection technique utilizes the mammary ductoscope and additional devices, such as a cytology brush or a tissue biopsy tool. The physician looks directly into the mammary ducts while doing cytology or tissue collection.

The destruction of the intraductal epithelia tissue can be performed by various energy delivering devices including cryotherapy, radiofrequency, microwave energy, bipolar radiofrequency energy, high frequency ultrasound, and laser energy. The Food and Drug Administration (FDA) has approved laser, cryo, ultrasound and RF energy for breast tissue ablation but such ablation is not currently being used within the breast ducts.

Attempts have been made to provide an instrument which will allow the taking of tissue samples within small duct areas. A simple double barrel catheter with adjacent lumens is disclosed in U.S. Pat. No. 6,221,622 with one of the lumens being used to irrigate the milk duct of a breast and the other lumen being used to aspirate the fluid which has entered the duct allowing a continuous flow of saline through the duct which hopefully carries enough cells and tissues for a biopsy. Problems in the use of such an instrument include the small size required by the narrow small diameter lumens which can be blocked or limit the flow of fluid back through the aspiration lumen and thus preclude significant tissue collection or cause duct collapse. While the '622 Patent shows a small lumen size, the size problem is magnified when the other existing prior art is attempted to be applied to breast ducts because of the small size and thin cell walls of the mammary ducts.

The ablation of tissue in various other regions of the body has been previously studied. U.S. Pat. No. 5,107,513 describes the general use of three types of lasers. Carbon dioxide ($CO_2$) laser radiation is intensely absorbed by water and thus acts as a surgical knife and vaporizer, its penetration depth in tissue being 0.03 mm. Argon lasers are minimally absorbed by water but intensely absorbed by hemoglobin and penetrate 1 to 2 mm in most tissue. These lasers are especially useful in coagulating bleeding points in small superficial vessels. Neodymium-Yttrium-Aluminum-Garnet (Nd:YAG) lasers are poorly absorbed by both water and hemoglobin. These lasers are able to penetrate large volumes of tissue, blood clots and coagulate large bleeding vessels. A Holmium laser with a 2100 nm wavelength has good cutting capabilities and its coagulating properties are similar to those of the Nd:YAG laser, penetrating to about 0.4 mm for most tissue. Likewise all of the previously noted energy ablation methods have been used surgically on human beings in much larger areas of operation.

Thus, there is a need in the art for new and better micro-cannula/endoscope assemblies and methods for using same that can be used to directly visualize the mammary ducts of a breast where visualization is by means of endoscopic devices, direct visualization (as opposed to creation of photographic images) and offers the additional advantage that the equipment required is comparatively simple to use and is less expensive than the equipment required to create photographic displays from such images. In addition, there is a need in the art for a method of ablating diseased or abnormal tissue which are located during such visualization within the mammary duct.

SUMMARY OF THE INVENTION

The present invention is directed toward the detection and treatment of abnormal growths and cancer located in the mammary ducts of women's breasts which in the present invention is when the cancer is typically between two and three years old with a size of about 0.2 mm. This is over 50 times more sensitive than a standard mammogram. According to the invention, an apparatus and a method is provided for ablating abnormal tissue found in the mammary duct using a micro-endoscope assembly having irrigation and aspiration capabilities. The micro-endoscope assembly includes a proximal actuation handle, an elongate flexible member extending from the proximal actuation handle and having an irrigation conduit, a probe located at the distal end of the endoscope or in the sheath cannula for application of a form of energy to a mammary duct site to ablate the tissue at the duct site.

The method comprises the steps of: inserting the cannula sheath in the duct of the breast of a woman, inserting the distal end of the micro-endoscope assembly into the sheath; viewing the inside of the duct as the distal end of the endoscope travels along the duct until a tissue abnormality is viewed; positioning the distal assembly proximate to a tissue to be sampled; ablating the tissue and/or cell from the tissue abnormality site using a form of energy eminating from a probe in the micro-endoscope; introducing irrigation and subsequently a negative pressure through a micro-endoscope conduit to transport ablated tissue out of the wound area.

It is another object of the invention to allow physicians to perform a variety of intraductal procedures with minimal or no discomfort for patients.

It is still another object of the invention to provide convenient, efficient, and economical mammary ductoscopy-breast care.

It is thus an object of the invention to provide a micro-endoscope assembly which can view the interior of a lactiferous duct to ascertain tissue abnormalities and ablate tissue at the site.

It is yet another object of the present invention to provide for the ablation of intraductal tissue with more precision and less trauma than by convention surgical procedures.

It is also a further object of the micro-endoscope assembly invention to provide for micro-endoscopic ablation using probes contained in the micro-endoscope.

It is still a further object of the micro-endoscope assembly invention to provide for micro-endoscopic ablation using probes contained in the cannula sheath.

It is an object of the present invention to provide surgical means for achieving rapid ablation by an ultrasonic surgical instrument that can be tailored to access internal mammary duct areas.

It is another object of the present invention to provide surgical means for achieving rapid ablation by a cryogenic surgical instrument that can be tailored to access internal mammary duct areas.

It is still another object of the present invention to provide surgical means for achieving rapid ablation by a radio frequency surgical instrument that can be tailored to access internal mammary duct areas.

It is an yet another object of the present invention to provide surgical means for achieving rapid ablation by a microwave surgical instrument that can be tailored to access internal mammary duct areas.

It is a further object of the present invention to provide surgical means for achieving rapid ablation by a bipolar electrode surgical instrument that can be tailored to access internal mammary duct areas.

It is an object of the present invention that it provides a practical high intensity focused ablation energy form that is easily usable and error resistant in intraductal surgery.

It is another object of the present invention to provide a medical instrument of high durability which is easily cleaned and sterilized.

It is also an object of the micro-endoscope assembly invention to create a micro-endoscope assembly which can be easily handled by the physician for intraductal surgery.

These and other objects, advantages, and novel features of the present invention will become apparent when considered with the teachings contained in the detailed disclosure which along with the accompanying drawings constitute a part of this specification and illustrate embodiments of the invention which together with the description serve to explain the principles of the invention.

BRIEF DESCRIPTION OF THE DRAWINGS

FIG. 1 is an exploded side elevational view of the endoscope used in the present invention;

FIG. 2 is an enlarged partial cross section of the lens end of the endoscope in FIG. 1;

FIG. 3 is a perspective orientated view of the back end of the endoscope showing a light post and laser post;

FIG. 4 is a perspective view of a portion of the front end of the micro-endoscope assembly;

DETAILED DESCRIPTION OF THE INVENTION

Figure 5:
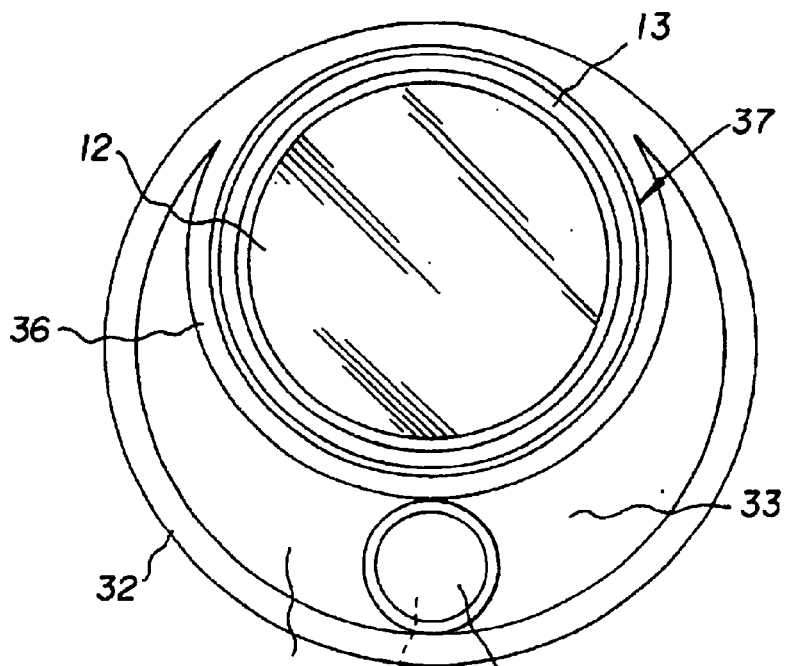
FIG. 5 is an enlarged cross sectional view taken along line 5'—5' on FIG. 4.

The present invention is directed towards a micro-endoscope assembly 10 which can be used and inserted into the lactiferous ducts of the breast of a woman patient and a method for intraductal cytology. The lactiferous ducts generally range in number from about six to about twelve in women and lead from areas of the breast to the nipple where they are in parallel vertical orientation with each other. The ducts have a very thin cell wall ranging from 3 to 4 cells in thickness and are resilient. The ducts have a smooth inner surface and white color which resemble visually the interior of a standard PVC pipe.

The best mode and preferred embodiment of the invention is shown in FIGS. 1–5. The micro assembly 10 consists of tube or guide cannula 14 which seats and guides the endoscope 12. The cannula 14 has an outer cylindrical wall 16 which defines an internal passageway which runs along its length to seat and guides the endoscope 12. Cannula tube 14 may be a rigid steel tube ranging from 5–20 cm long having an outer diameter ranging from 0.5 mm to approximately 1.2 mm or alternatively may be a semi-rigid tube made of flexible or transparent plastic, or some other suitable material, and having the same or a longer length. The exterior of the cannula is marked with marking indicia 15 as seen in FIG. 4 so that the depth of penetration of the micro-endoscope assembly into the duct can be noted. The marking indicia can be in the form of rings of opaque, translucent or light reacting material or any other suitable geometry which is easily visible to the surgeons eye. The marking indicia can be printed onto the outer surface of the cannula or imbedded in the cannula structure material. Various cannula are envisioned to be interchangeable with the endoscope 12 by unscrewing one guide cannula from the endoscope front hub 18 and its associated connector member 20 and screwing one another on to the connector member.

The endoscope 12 is provided with tube body 17 formed with objective lens 22 at its distal end and image guide 24 as is more clearly shown in FIG. 2. The endoscope 12 has a proximal end in the form of a back member 26 having a light post 27 and a video port 29 as seen in FIG. 3.

The preferred cannula embodiment 30 has a cylindrical outer cannula or sheath 32 formed with a beveled distal end 34 as shown in FIG. 4 or a cylindrical end as shown in FIG. 2. The inner wall of sheath 32 defines a cylindrical inner channel 33 which has an inner cylindrical tube 36 eccentrically mounted thereon. The tube 36 defines the endoscope channel 37 and holds endoscope 12. The inner cylindrical tube 36 is eccentrically mounted in cylindrical inner channel 33 to the wall of the cannula sheath 32 and its outer surface together with the inner surface of the sheath or tube 32 to define a moon shaped channel 38 which acts as a channel or passageway providing irrigation and aspiration and is also used as a port through which an ablation probe 60 can be inserted until it reaches the patient's duct area containing cells and/or tissue showing abnormal characteristics.

Suitable working devices in the form of micro-probes 60 that can be inserted in the working channel 38 of the micro-endoscope include energy delivery probe devices which include laser wave guides, RF electrodes, microwave cutters, ultrasound transmitters and cryogenic ice formers. The generator or energy source for each form of energy is indicated by block diagram 64.

Each energy delivery probe 60 is preferably surrounded by an insulation layer 62 and the probe is configured to be coupled to an energy generating source generator 64 including but not limited to RF, laser, microwave, ultrasound, cryogenic fluid, chemical ablation and the like. The distal portion of the working endoscope device allows the probe energy delivery device to be positioned either contacting or in close proximity to an abnormal tissue site inside the duct while energy is delivered through the energy delivery device. The scopes distal end via the probe thus allows energy to be delivered to the abnormal tissue site with minimal surrounding tissue destruction.

Cryoablation is a technique in which a cryoprobe 70 is inserted through the passageway and into the mammary duct. The probe is cooled either by liquid nitrogen or by differential gas exchange (described by Joule-Thompson). In most Joule-Thomson systems 200, single non-ideal gasses are pressurized and then expanded through a throttling component or expansion element, to produce isenthalpic cooling. The characteristics of the gas used, such as boiling point, inversion temperature, critical temperature, and critical pressure determine the starting pressure needed to reach a desired cooling temperature. Joule-Thomson systems typically use a heat exchanger to cool the incoming high pressure gas with the outgoing expanded gas, to achieve a higher drop in temperature upon expansion and greater cooling power. For a given Joule-Thomson system, the desired cooling dictates the required heat exchanger capacity.

Smaller heat exchangers have also been known, constructed of photo-etched glass plates. These heat exchange systems are still in the range of several centimeters square in size, making them still too bulky for true micro-miniature use, such as in endoscopes. Further, these heat exchangers are planar and difficult to incorporate into tubular structures such as catheters or endoscopes. Heat exchanger requirements can be reduced by pre-cooling the gases prior to the probe tip heat exchanger. This can be done by incorporating a Peltier device in the flow path prior to the probe tip heat exchanger. Gas flowing through a heat exchanger on the surface of the cold side of the Peltier device would be cooled prior to reaching the probe tip heat exchanger. Alternatively, the inlet high pressure stream could be split so that a portion of the stream could be diverted and expanded to cool the remaining portion of the inlet stream prior to reaching the probe tip heat exchanger.

Increased cooling in Joule-Thomson systems can be realized by using a mixture of gasses rather than a single gas. For example, the addition of hydrocarbons to nitrogen can increase the cooling power and temperature drop for a given inlet pressure. Further, it is possible to reduce the pressure and attain performance comparable to the single gas system at high pressure. Similar to single gas systems, these mixed gas systems have heat exchanger requirements and are limited in their miniaturization potential by the size of the heat exchanger. The improvement in cooling performance realized by mixed gas systems is very desirable for medical microminiature systems.

Small probes can now be used by pre cooling the primary fluid mixture with a secondary closed loop Joule-Thomson refrigeration cycle to maximize the available cooling power of the fluid mixture.

The microminiature heat exchanger in the cold tip can be a single coiled tube 74 surrounded by a low pressure return passageway and enclosed in an insulated sheath 72. Alternatively, it can have a laminated construction of several different types. In one example of the laminated type, the microminiature heat exchanger is constructed of a plurality of plates and spacers stacked alternately along the axial dimension of the heat exchanger. The plates have a first set of holes establishing the high pressure passageway of the heat exchanger, and a second set of holes establishing the low pressure passageway of the heat exchanger. The high pressure holes are segregated from the low pressure holes. Spacers with larger openings are stacked between the plates to promote turbulent flow and insure effective heat exchange. The plates and spacers can be fastened together by a process such as diffusion bonding. The primary and secondary Joule-Thomson expansion elements can be a sintered metal plug made by sintering a number of metal beads into a metal cup, to provide the required pressure drop. Alternatively, the expansion element can be a properly sized orifice or some other type of restriction. The two different stages of the sintered plug expansion element, if present, can utilize different sizes of beads, different cross sectional areas, and different packing densities. The heat transfer element can take the optimum shape for matching the object or tissue to be cooled. For example, a metal plug can be installed in the tip of the outer tube or catheter, for applying cooling through the extreme distal tip of the catheter. Alternatively, a relatively narrow metal strip can be mounted in a side wall of the catheter, near the distal tip, for applying cooling to a narrow strip of tissue. The severe limitation on the size and capacity of the cold tip heat exchanger dictates that the system be optimized by selection of a gas mixture which will have the appropriate thermodynamic properties to perform as well as possible. The goal of this selection process is to maximize the cooling power of the combination of the pre-cooling heat exchangers, the cold tip heat exchanger, and the primary Joule-Thomson expansion element. For a given gas mixture operating between selected high and low pressures and between selected high and low temperatures, there is a limit to the amount of heat which can be transferred, even in a perfect heat exchanger. The best use of the apparatus of the present invention requires a method for selecting, from among a group of gas mixture candidates, a mixture which will maximize the performance ratio between the cooling power of the Joule-Thomson expansion element and the heat transfer capacity of a perfect heat exchanger. Selections of gas mixtures and tip construction and materials is taught in U.S. Pat. No. 5,758,505 issued Jun. 2, 1998 which is incorporated herein by reference.

In the present invention an elliptical ice ball approximately 1-centimeter in diameter forms around the probe tip 70 when it is cooled to less than −90 degrees Celsius. At the edge of the ice ball, the tissue temperature is 0 degrees Celsius, which is nondestructive. A temperature of −20 degrees Celsius is lethal to tissue; this temperature is reached approximately 0.5 cm from the edge of the ice ball. Therefore, the intraductal tissue exposed to this low temperature, including the epithelial layer is permanently destroyed. The number of ice balls that must be created to destroy an entire ductal segment is dependent upon the size of the lesion or abnormality. In general, two to three ice balls are sufficient. The entire procedure can take up to 10 to 30 minutes depending upon the size of the lesion.

The primary advantage to cryoablation is that it is not a totally blind procedure. The ice ball created can be followed by breast ultrasound and when the edge of the ice ball approaches the outside of the mammary duct, the procedure can be stopped. This visual feedback also facilitates complete ablation of the entire lesion and is not dependent upon the duct size. In addition, freezing tissue causes less pain (e.g., cryoanesthesia) than heat energy associated with all the other ablation devices.

Because cryotherapy produces a local anesthesia, the cryoablation techniques should produce the least amount of pain.

Figure 7:
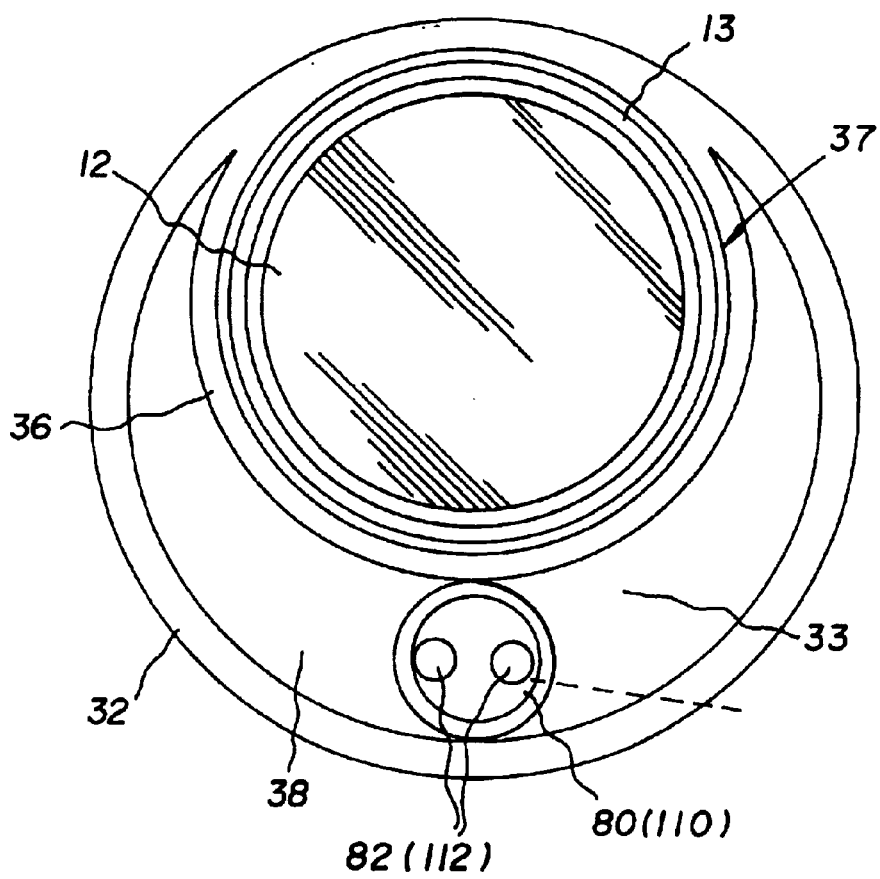
FIG. 7 is an enlarged cross sectional view taken along line 5'—5' on FIG. 4 showing several aspects of the invention.

Bipolar Desiccation Ablation—An electrode deployment probe 80 as seen in FIG. 7 is positioned within passageway 38, and includes a plurality of electrodes 82 that are retractable in and out of distal end of the probe 80. Electrodes 82 can be of different sizes, shapes and configurations. In the preferred embodiment, they are needle electrodes. The electrodes 82 are in non-deployed positions while retained in micro-endoscope. In the non-deployed positions, electrodes 82 may be in a compacted state, spring loaded, generally confined or substantially straight if made of a suitable memory metal such as nitinol or titanium. As electrodes 82 are advanced out of distal end of the probe 80 they become distended in a deployed state, which defines an ablative volume, from which tissue is ablated. Electrodes 82 operate either in the bipolar or monopolar modes. When the electrodes are used in the bipolar mode, the ablative volume is substantially defined by the peripheries of the plurality of electrodes 82. The cross-sectional width of the two electrode wires may be employed alternatively in bi-polar mode for localized measurements. The probe 80 converts electrical signals into specific motion inside the mammary ducts. In another embodiment a mesh construct is expanded until the pressure insuring intraductal contact is met. Alternately a balloon having interwoven mesh can be used. Suction is applied to the intraductal cavity when the mesh construct is used, thereby drawing it closer to the bipolar mesh probe or the balloon is expanded accomplishing the same purpose.

The bipolar generator 202 applies up to 180 watts of energy. The system will shut down when complete desiccation (calculated at 50 ohms of resistance) has occurred. The average treatment time is just over one minute and the average depth of ablation is 4 to 5 millimeters.

Microwave Ablation—A sheathed probe 90 as seen in FIG. 5 with a 9.2 GHz, 30 watt, microwave generator 204 is used to produce a tissue temperature of 95 degrees Celsius at a depth of 6 mm when inserted in tissue. In order to treat the epithelia tissue within the mammary duct, the surgeon moves the probe within the mammary duct along the targeted lesion until the entire lesion has reached the desired temperature of 95 degrees Celsius. Total treatment time is 2 to 5 minutes. Unlike other ablation devices, the probe is reusable and can be sterilized in the autoclave or with liquids.

In the cryogenic, microwave, radio frequency and bipolar electrode energy sources noted above an insulator sleeve can be formed around the probe or electrode(s) or adapted to be advanced along a desired length of electrode after electrode has been positioned adjacent around a targeted mass to be ablated. The insulator sleeve is thus capable of advancing with the electrode or it can move through tissue without electrode providing the source of movement. Thus, the desired ablation volume is defined by deployed electrodes, as well as the positioning of insulator sleeve on each electrode. In this manner, a very precise ablation volume is created. Suitable materials that can be used to form the insulator sleeve include but are not limited to nylon, polyimides, other thermoplastics, and the like.

Figure 8:
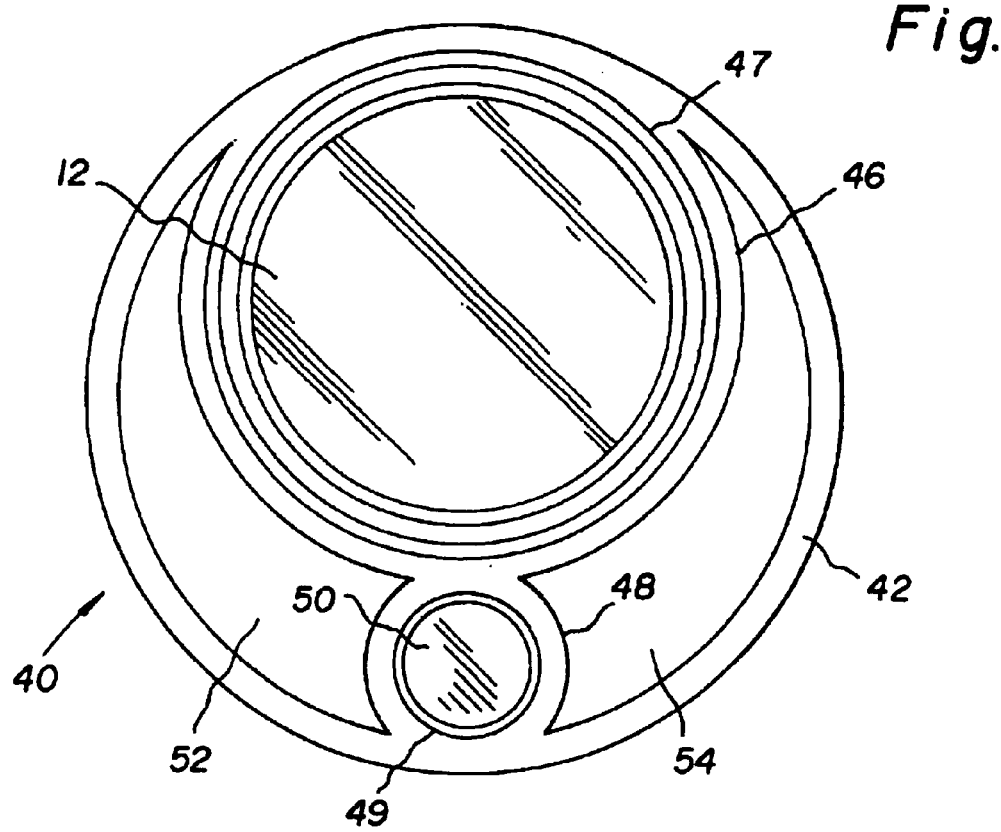
FIG. 8 is an alternate embodiment of the micro-endoscope assembly invention.

Laser Ablation A laser fiber 100 as seen in FIG. 5 and in FIG. 8 comprising a 21 W diode laser can be used to ablate a lesion within the mammary duct. One laser system called GyneLase and is manufactured by ESC/Sharplan (Needham MA/Israel). This diode laser has a wavelength of 830 nm and is applied with a fiber IUD-like device. The folded fibers have an insertion diameter of 6 mm, the two lateral fibers have a 3 cm diffusion length, and there is a 4 cm diffusion length on the middle fiber. Each fiber delivers 5 to 7 W of power. The entire cavity is illuminated for 7 minutes. The programmed laser delivers 20 W in the first 90 seconds, 18 W in the second 90 seconds, and 16 W in the final 240 seconds.

The mammary duct can be treated by light diffusion, which utilizes heat instead of direct intraductal contact. Therefore, this technique is more likely to be useful in slightly distorted ducts. The 6 mm introducer also makes it a reasonable office procedure. The diode laser itself is small (slightly larger than a portable notebook computer) and much less expensive that other laser technologies.

Ultrasonic Ablation—A probe 110 as alternately seen FIG. 5 is comprised of a portable generator, hand piece and single patient contact small diameter probe. The probe has an overall length and a small diameter suitable to easily fit in the sheath or micro-endoscope. The generator controls the ultrasonic power level, measures the total treatment time and the hand piece converts the energy from the generator 204 to the specially tuned probe 110. The probe generates an ultrasonic wave 360 degrees around the probe and the probe is constructed of a titanium alloy and is operated for up to 30 second intervals. The acoustic energy is transmitted down the probe and resonate around its length. The unshielded portion of the probe produces micro-shock waves that ablate tissue in an effective ablation zone of 6 mm in diameter. The ultrasonic waves disrupt the cell walls and tissue matrix causing the breakdown of the same into micro-particles which can be irrigated and the resulting particles are drawn out of the cannula.

Figure 6:
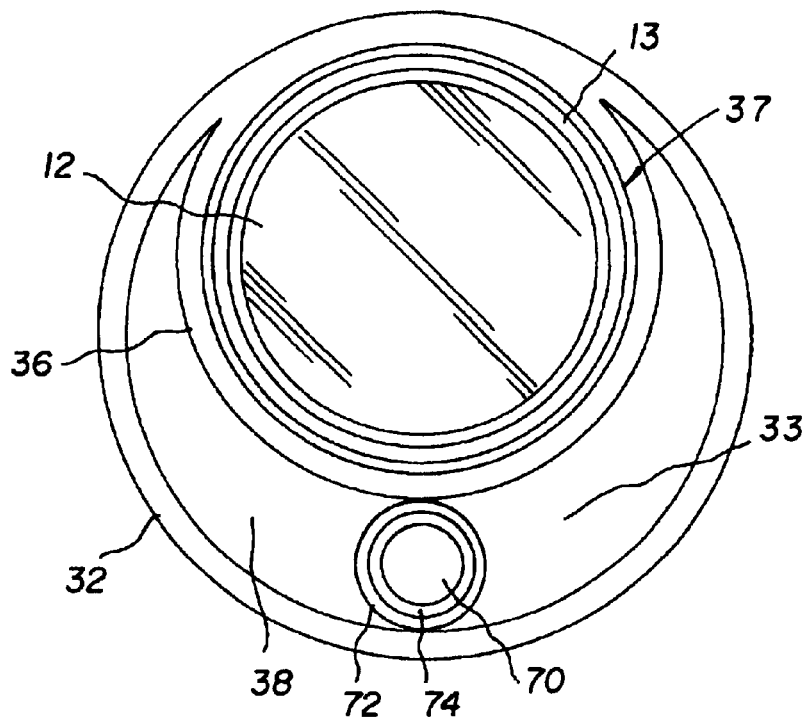
FIG. 6 is an enlarged cross sectional view taken along line 5'—5' on FIG. 4; showing several aspects of the invention.

Radiofrequency Therapy—A probe 120 as alternately seen in FIG. 6 is provided with radio frequency electrodes 112. An RF electrosurgery probe 120 passes through the passageway 38. Within the housing, a socket end is positioned adjacent a RF-wire channel that passes through the axis of the cone. A replaceable RF tip can be inserted through the channel into the socket end and then protrudes from the cone-tip into the tissue. The probe 120 can be inserted through the cannula, which is placed within the mammy duct. The electrodes are heated to 70 degrees Celsius for four minutes using 45 W of power from an electrically connected RF generator 206.

An advantage of radio frequency ablation is that it is very simple to learn and is an excellent tool for physicians with little expertise in operative RF technology.

High Frequency Ultrasound Ablation—The ultrasound probe applicator 130 as alternatively seen in FIG. 5 is fabricated of a solid material with low acoustic attenuation and accoustically coupled to an ultrasound generator 208. Materials suitable for medical application include ceramic, glass, fused quartz, and metal, with a preference for ceramic as ceramic piezoelectric transducers are commonly used in medical ultrasound. Thus, a ceramic applicator offers excellent acoustic matching to a ceramic-type transducer without the need for intervening matching layers. Steel, silver, aluminum, and zinc also offer good acoustic matching properties and will be less expensive than ceramic or glass. A glass applicator, such as of crown glass, offers the least suitable impedance matching option, but offers the possibility of a see-through device which would be advantageous during a surgical procedure. The present invention provides a high intensity focused ultrasonic applicator device for performing medical procedures, including: at least one transducer for generating a focused ultrasound beam; a coupler, or applicator, which transmits the beam towards a focal point therein; the coupler is formed of a solid material; and a lens mechanism, located between the transducer and the focal point, for redirecting the beam. The concave tip acts as an acoustic lens whereby very high acoustic intensities can be generated at the focal region of this applicator lens-tip. By altering the radius of curvature of the transducer or the applicator lens-tip different focal lengths,(Lf), reaching different depths from the tip into the tissue, are achieved. Thus, either the diameter of the transducer or the dimensions of the applicator may be altered to produce a variety of implementations. The gain in intensity of the ultrasound generated by the transducer is equal to the surface area of the transducer element divided by the surface area of the truncated tip. Absorption in the tissue is a direct function of frequency; i.e., the higher the frequency the faster the absorption. Thus, a specific implementation can be tailored by transducer and cone geometry and selected transducer frequency frequency. It has been found that ultrasonic frequencies in the range of approximately 2–10 MHZ are preferred in HIFU medical procedures, although a range of 0.5 to 100 MHZ may be used for specific implementations. The resolution of the transducer increases with increasing frequency, thus allowing smaller effective focal region volumes. Higher frequency energy is absorbed more readily and can produce faster cauterization, but attenuates rapidly and thus has a short range of effectiveness. Thus, operating frequencies are chosen based upon the desired treatment depth, transducer and focused-beam geometries. The transducer diameter must be large enough to produce a power level necessary for tissue destruction. The handle is adapted for providing a conduit for coupling power and a cooling medium to the cavity.

Electrical signals may be used in a thermocouple or thermistor mounted near the tip to sense temperature at the tip. Alternatively, electrical current (e.g. at 100 KHz) to measure the tissue electrical impedance can allow detection when tissue is in contact—turning on and off the unit automatically when it is in contact and not in contact, respectively, based on the impedance change. Further, the tissue electrical impedance will change with temperature. Therefore, as the ultrasound energy heats it up the electrical impedance change can be used to indicate therapeutic action is being achieved and therefore provide feedback to the user or directly to the unit to control the energy delivery. In this mode, a single wire with an electrode at the tip may act as monopolar impedance electrode measuring impedance against a common electrode located elsewhere on the body. Monopolar impedance measurement methods are well known in the state of the art.

The motion of the probe causes "cavitation", which can be described as a "cold boiling" of water—the motion of the probe causes the formation of micro bubbles. As these bubbles are broken, they cause a focused shock wave that ablates the tissue in a controlled fashion. Single patient ultrasonic probes provide means to both ablate and aspirate tissue from the surgical site. Small diameter, flexible probes are designed to mimic conventional surgical instrument patterns while removing large volumes of tissue.

An alternate embodiment of the cannula 40 is shown in cross section in FIG. 8. This embodiment has a cylindrical outer cannula or sheath 42 which defines a cylindrical inner channel 43 in which an inner cylindrical tube 46 is eccentrically mounted to the wall of sheath 42. The cylindrical tube 46 defines the endoscope channel conduit 47 to hold the endoscope 12. A second smaller cylindrical tube 48 is eccentrically mounted in channel 43 adjacent to and integral with a portion of the wall of tube 46 and a wall of the cannula 42 to form an ablation probe channel 49 which holds the ablation probe 60. The cylindrical tube structure 46 divides the moon shaped channel up into two separated segments 52 and 54 which serve as the irrigation and aspiration channels for the assembly. Any of the specific energy form ablation probes previously discussed can be used in place of probe 60.

FIG. 1 also shows the endoscope 12 with the lens tube 17 and tube portion 19 coupled between hub 18 and back end 26. Tube 19 includes a passageway in it's interior capable of holding fiber optic strands and/or illumination strands. Such strands run from video port 29, through tube portion 19 into hub 18. The strands run through hub 18 into the inner passageway of tube portion 17 though or outside of the working channel, as described in more detail below. These strands provide both a light source to the area of interest and a video source to the video port, allowing the physician to see an image of the area of the duct in which ablation is to be under taken. The back end 26 is formed with a light source post connector 27. The tube portion 14 which has an outer diameter of approximately 1.2 mm has a working channel, a plurality of light fibers and a lens 22. The light fibers 22 run the length of the guide tube 17 and provide light to the areas of interest. The light fibers are commercially available. The tube cannula 14 can alternately carry the light fibers or have them molded in the tube material. The lens 22 also runs longitudinally down inner passage of guide tube 17. The laser fiber 50, 82 transmits the laser energy out the distal end of the endoscope via the contact laser tip to the surgical site. Suitable lasers which can be used with the invention are manufactured by Surgical Laser Technology, Inc.

Because the cannula tube is of such a small outer diameter, the physician can manipulate the tube from the proximal end in order to place the end of the tube with the ablation probe 60 projecting therefrom adjacent the diseased tissue.

The endoscope 12 is used in conjunction with a video monitor and prismatic screen (not shown). The video port 29 is coupled to a video camera which is in turn coupled to a video monitor as is well known in the art and has an attached prismatic screen manufactured by Acueity Inc. The video camera may be of many different commercially available models, although CCD cameras are particularly useful in this type of application. Specifically, a Panasonic GS99-NTSC medical video endoscopy camera, from Matsushita Electric Corporation of America, has been found to be useful. Moreover, it has been found that in such a camera ¼ inch CCD chip is more advantageous than a ½ inch CCD chip, because it provides an image with smaller pixels. Such chips are included in CCD cameras and also are commercially available from many sources such as, for example, the Sony Corporation of America. The video monitor may be any of a number of commercially available video monitors.

It is not necessary to include a prismatic screen to use the endoscope of the present invention. However, the use of such a screen is advantageous because, as described above, the screen provides an image with increased clarity and perception of depth by causing the brain of the viewer to interpret depth cues present in the image. This increased perception of depth is particularly advantageous in medical procedures like those that employ endoscopes because of the small dimensions involved and the limited lighting available in the interior of a patient's body.

In operation of the micro-endoscope assembly 10, the rigid guide tube 14 is placed in a lactiferous duct in the patients breast after the nipple has been numbed. The physician can view the interior of the duct, which has a white smooth surface, as the endoscope passes on its way through the duct to the area of interest which has an abnormal appearance and is found by watching the screen attached to video monitor. Once the duct area of interest is reached, the physician can manipulate the biopsy tube end 35 to orient the energy probe adjacent the tissue to be ablated. The energy generator is activated to pass specified energy through the probe and ablate the duct tissue. Ablated tissue is then irrigated and removed from th duct site through a working channel in the micro-endoscope assembly.

The principles, embodiments and modes of operation of the present invention have been described in the foregoing specification. The invention that is sought to be protected herein, however, is not to be considered as limited to the particular forms disclosed, since these are to be regarded as illustrative rather than restrictive. Variations and changes may be made by those skilled in the art without departing from the spirit and scope of the invention. For example, the present invention is not limited to the particular dimensions or uses described, except as explicitly defined in the claims. Instead, the embodiments described here should be regarded as illustrative rather than restrictive. Variations and changes may be made by others without departing from the scope of the present invention as defined by the following claims.

What I claim is:

1. A micro-endoscope assembly for the ablation of tissue from inside breast ducts comprising a cylindrical guide tube having a diameter ranging from 0.5 mm to about 1.2 mm and having an inner wall surface defining an internal cylindrical passageway, a smaller cylindrical tube eccentrically formed in said cylindrical passageway of a smaller diameter than said tube internal cylindrical passageway to receive and guide an endoscope with a handle assembly, said smaller cylindrical tube including an outer wall surface wherein a portion of said outer wall surface is unitary with a portion of the inner wall surface of the cylindrical guide tube, the outer wall surface of the smaller cylindrical tube forming together with the inner wall surface of said cylindrical guide tube at least a second passageway, an endoscope in said smaller cylindrical tube, said at least one second passageway defining a moon shaped port in vertical cross section adapted to provide irrigation and aspiration and further adapted to receive an ablation probe, the probe being mounted for side-to-side movement within said port.

2. A micro-endoscope assembly as claimed in claim 1 wherein said ablation probe is cryogenic and creates a temperature of at least 20 degrees Celsius.

3. A micro-endoscope assembly as claimed in claim 1 wherein said ablation probe provides bipolar desiccation.

4. A micro-endoscope assembly as claimed in claim 1 wherein said ablation probe distributes microwave energy.

5. A micro-endoscope assembly as claimed in claim 1 wherein said ablation probe is a laser fiber.

6. A micro-endoscope assembly as claimed in claim 1 wherein said ablation probe has at least one radio frequency electrode.

7. A micro-endoscope assembly as claimed in claim 1 wherein said ablation probe distributes ultrasound energy.

8. A micro-endoscope assembly as claimed in claim 1 wherein said ablation probe distributes ultrasonic energy.

9. A micro-endoscope assembly for the ablation of tissue from the interior of breast ducts comprising a cylindrical guide tube having a diameter ranging from 0.5 mm to about 1.2 mm and having an inner wall surface defining an internal cylindrical passageway, a first cylindrical tube eccentrically formed in said internal cylindrical passageway of a smaller diameter than said guide tube internal cylindrical passageway to receive and guide an endoscope with a handle assembly, said smaller cylindrical tube including an outer wall surface a portion of which is unitary with a portion of the inner wall surface of the cylindrical guide tube, the outer wall surface of the smaller cylindrical tube forming together with the inner wall surface of said cylindrical guide tube at least a second passageway, and an endoscope mounted in said first cylindrical tube, said cylindrical guide tube having a second cylindrical tube of a smaller diameter than the first cylindrical tube positioned between the first cylindrical tube and the inner wall surface of said cylindrical guide tube, said second cylindrical tube having an outer wall surface, opposed portions of which are unitary with a portion of the outer wall surface of the first cylindrical tube and a portion of the inner wall of said cylindrical guide tube respectively and dividing said at least second passageway into two separate divided ports adapted to provide irrigation and aspiration, and an ablation probe moveably mounted within said second cylindrical tube.

10. A micro-endoscope assembly as claimed in claim 9 wherein said ablation probe is cryogenic and creates a temperature of at least 20 degrees Celsius.

11. A micro-endoscope assembly as claimed in claim 9 wherein said ablation probe provides bipolar desiccation.

12. A micro-endoscope assembly as claimed in claim 9 wherein said ablation probe distributes microwave energy.

13. A micro-endoscope assembly as claimed in claim 9 wherein said ablation probe is a laser fiber.

14. A micro-endoscope assembly as claimed in claim 9 wherein said ablation probe has at least one radio frequency electrode.

15. A micro-endoscope assembly as claimed in claim 9 wherein said ablation probe distributes ultrasound energy.

* * * * *